(12) United States Patent
Wickland et al.

(10) Patent No.: US 6,935,199 B2
(45) Date of Patent: Aug. 30, 2005

(54) HEADSPACE GAS SAMPLING AND VENTING METHOD AND ARRANGEMENT, AND FILTERING AND SAMPLING PORTS USED THEREWITH

(75) Inventors: Terry J. Wickland, Evergreen, CO (US); Darold M. Popish, Golden, CO (US); Gilbert Brassell, Golden, CO (US); Fred L. Popish, Arvada, CO (US); Mark A. Castagneri, Arvada, CO (US); Michael D. Peterson, Parker, CO (US)

(73) Assignee: Nuclear Filter Technology, Inc., Golden, CO (US)

( * ) Notice: Subject to any disclaimer, the term of this patent is extended or adjusted under 35 U.S.C. 154(b) by 0 days.

(21) Appl. No.: 10/299,911

(22) Filed: Nov. 20, 2002

(65) Prior Publication Data

US 2003/0101830 A1 Jun. 5, 2003

Related U.S. Application Data

(62) Division of application No. 09/922,943, filed on Aug. 7, 2001, now Pat. No. 6,557,428.

(51) Int. Cl.$^7$ ................................................ G01N 1/00
(52) U.S. Cl. ..................................... 73/864.74; 83/660
(58) Field of Search ......................... 73/863.23, 863.81, 73/864.74; 30/277, 165, 314, 119; 83/660; 141/329; 220/367.1, 368, 369, 370, 371, 372, 373, 374

(56) References Cited

U.S. PATENT DOCUMENTS

| | | | |
|---|---|---|---|
| 1,930,182 A | * | 10/1933 | Richardson ................. 152/506 |
| 3,872,730 A | | 3/1975 | Ringrose et al. |
| 4,545,440 A | * | 10/1985 | Treadway ................... 173/132 |
| 4,589,185 A | | 5/1986 | Schneider |
| 4,756,852 A | | 7/1988 | Temus |
| 4,766,923 A | | 8/1988 | Roper |
| 4,820,097 A | | 4/1989 | Maeda et al. |
| 4,969,787 A | | 11/1990 | Baars |
| 5,080,542 A | | 1/1992 | Sheahan |
| 5,131,283 A | | 7/1992 | Canfield |
| 5,193,709 A | | 3/1993 | Brassell |
| 5,634,484 A | | 6/1997 | Vodila et al. |
| 5,635,653 A | * | 6/1997 | Wittig et al. ............. 73/864.74 |
| 5,727,707 A | * | 3/1998 | Wickland et al. ........... 220/288 |
| 5,891,223 A | | 4/1999 | Shaw et al. |
| 5,928,468 A | | 7/1999 | Tolson |
| 6,041,669 A | | 3/2000 | Brassell et al. |
| 6,293,163 B1 | * | 9/2001 | Johnston et al. ......... 73/864.74 |
| 6,395,050 B1 | | 5/2002 | Wickland et al. |

* cited by examiner

*Primary Examiner*—Robert Raevis
(74) *Attorney, Agent, or Firm*—Millen, White, Zelano & Branigan, P.C.

(57) ABSTRACT

A headspace gas sampling and venting method utilizes a vent port and a sampling port which are punched through the lid of a drum containing hazardous materials, such as transuranic waste. In accordance with the system, a punch having a hollow passage therethrough, which passage has a filter element therein is first inserted through the lid using a pneumatic gun. A second punch, similar to the first punch, but having a passage with a septa seal therein is thereafter inserted through the lid with the pneumatic gun. Headspace gas beneath the lid is then sampled with a needle inserted through the septa seal. Both the venting port and sampling port are configured with detachable punch points which pass through the lid and are then released from the venting and sampling ports so as to open ends of the passages therethrough for communication with the headspace. In a preferred embodiment of the invention, the punch points are held on the venting and sampling ports by annular plastic retainers which break when the ports are inserted through the drum lid, thus allowing detachable punch points to fall away.

20 Claims, 3 Drawing Sheets

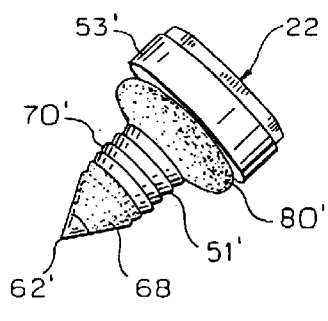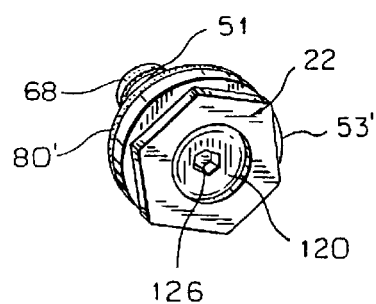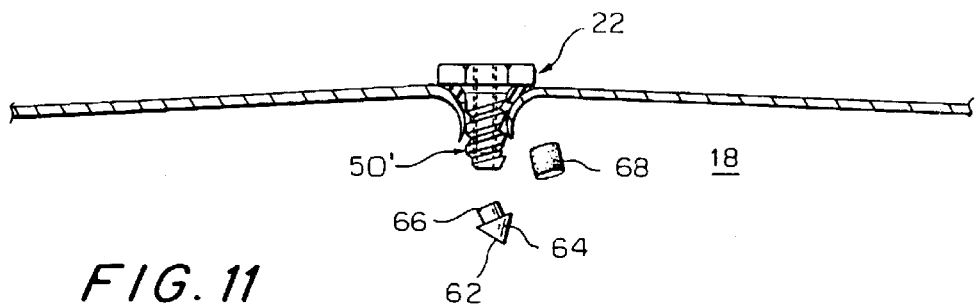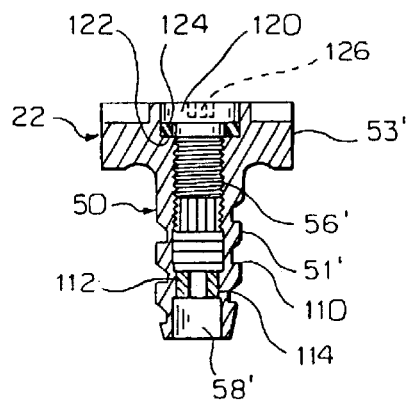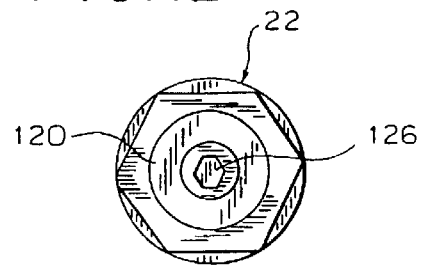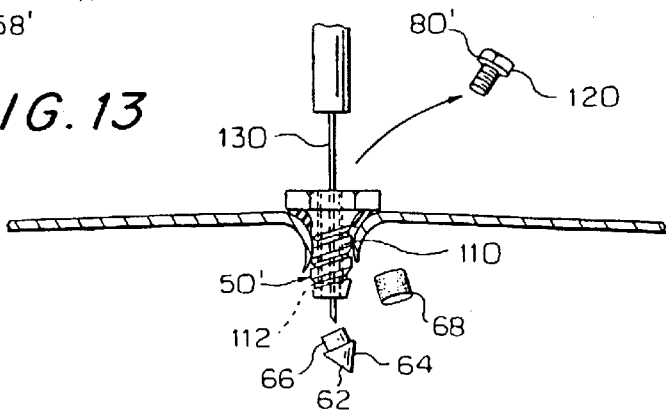

US 6,935,199 B2

HEADSPACE GAS SAMPLING AND VENTING METHOD AND ARRANGEMENT, AND FILTERING AND SAMPLING PORTS USED THEREWITH

RELATED PATENT APPLICATIONS

This application is a divisional application of U.S. patent application Ser. No. 09/922,943, filed Aug. 7, 2001, now U.S. Pat. No. 6,557,428.

FIELD OF THE INVENTION

The present invention is directed to a headspace gas sampling method and arrangements and filtering and sampling ports used therewith. More particularly, the present invention is directed to such method, arrangements and ports which are particularly suitable for sampling and filtering gases from waste material stored in containers, such as drums, wherein the material is a hazardous waste such as, but not limited to, transuranic waste.

BACKGROUND OF THE INVENTION

Since 1970, transuranic waste material generated in the United States by the Department of Energy Operations has been packaged in unvented, 55-gallon steel drums, which drums have been stored with the intention of future retrieval. It is intended that the material in these drums will be disposed of permanently in the Department of Energy Waste Isolation Pilot Plant (WIIP) Facility. Currently, there are safety concerns regarding these stored drums because of the potential presence of combustible headspace gases. These gases can include hydrogen and methane, resulting from the radiolytic decomposition of hydrogenous waste materials, e.g. paper, plastics and moist materials and/or from the presence of small amounts of combustible volatile organic compounds (VOCs) that are co-contaminants of transuranic waste. Future transportation and storage of these wastes stored in drums such as 55-gallon drums must address what is to be done about these gases.

The WIPP facility has waste acceptance criteria that requires that all packages stored must be vented. Moreover, those packages which are to be shipped to the Waste Isolation Pilot Plant must be vented and demonstrated to meet combustible gas concentration limits before shipping.

In addition, it is necessary that these drums retain their integrity during shipment in case the drums are accidentally dropped or are involved in a road or railway accident during shipment. Since there are millions of these drums, it is assumed that there will be accidents or occurrences that may stress the drums and increase the risk of spills or leaks. It is therefore important that any sampling ports or filter ports not be dislodged so as compromise the integrity of the drums.

Moreover, since the drums must be sampled and filtered, it is desirable that the sampling and application of filters be performed in an expeditious and safe manner.

SUMMARY OF THE INVENTION

In view of the aforementioned considerations, the present invention is directed to a drum sampling and filtering arrangement wherein a sampling punch and a filtering punch are used for each drum, the sampling and filtering punches being inserted by remote control using a remotely activated drive.

In a more specific aspect, the remotely activated drive is a pneumatic gun which drives the filtering punch and then the sampling punch through the lid of the drum at spaced locations through the lid.

In a further aspect of the invention, a punch is configured for penetrating a wall to access a space behind the wall, wherein each punch comprises an annular body having first and second ends for passage therethrough, the passage having a first opening and a second opening. The punch point is coupled detachably the first end of annular body. The coupling releases the punch point upon inserting the punch point through the wall, whereby the first opening of the passage communicates with the space behind the wall. In accordance with a preferred arrangement, the coupling comprises a deformable element which releases the punch point upon the punch point being forced through the wall. In a more specific aspect of the invention, the coupling comprises a stud on the punch point which is received in the open end of the passage, the punch point being held in the passage by an element which releases the punch point after the punch point has penetrated the wall. In a still more particular aspect of the invention, the element which holds the stud of the punch point in the passage is a collar which disengages from the punch point as the punch point passes through the wall.

In accordance with one embodiment of the punch, the passage includes the septa seal therein adapted to permit the passage of a hollow needle therethrough to sample in the space behind the wall. In accordance with another embodiment of the punch, the passage has a filter element associated therewith, wherein any fluid which passes from the first opening in the body and through the second opening in the body must pass through the filter element.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein:

FIG. 8 is a top perspective view of a sampling port configured in accordance with the present invention;

FIG. 9 is a side perspective view of the sampling port of FIG. 8;

FIG. 10 is a side view of the sample port of FIG. 9 installed through a wall of the container of FIGS. 1 and 8;

FIG. 11 is a side elevation of the sample port of FIGS. 8–10;

FIG. 12 is a top view of the sample port of FIGS. 8–11, and

FIG. 13 is a side view similar to FIG. 10 but showing a needle withdrawing head space gas.

DETAILED DESCRIPTION

Figure 1:
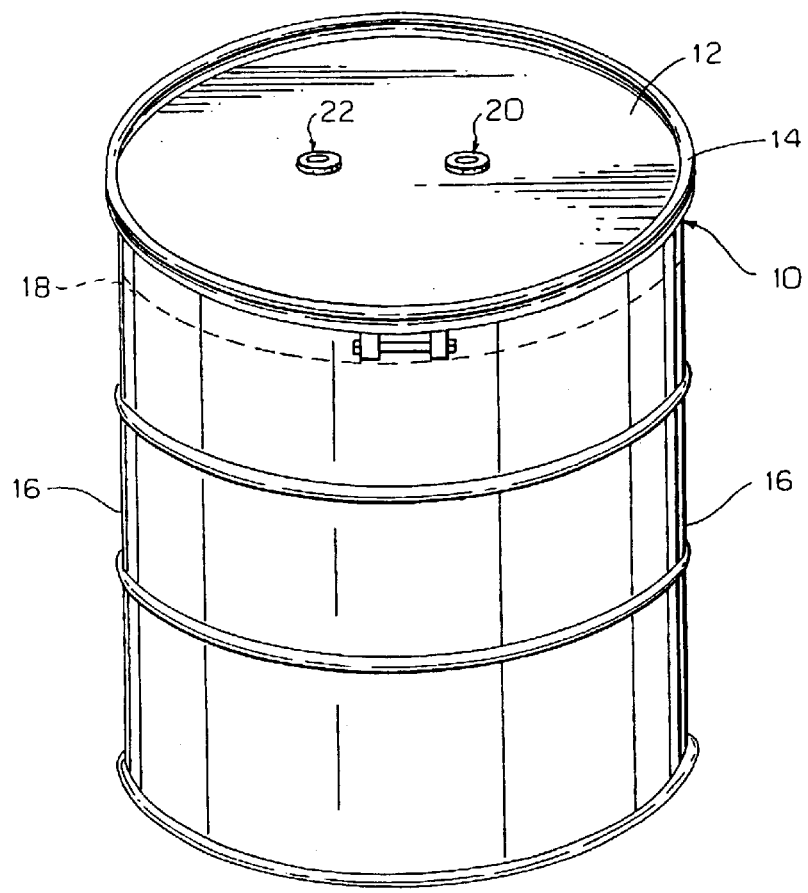
FIG. 1 is a side perspective view of a container having a lid with a sample port and a filter port disposed therein.

Referring now to FIG. 1, there is shown an arrangement in accordance with the present invention wherein a container, such as a 55-gallon steel drum 10, having a circular lid 12 formed about an axis 13 retained thereon by circular clamp 14, is used to store waste such as transuranic waste 16. Between the transuranic waste 16 and the lid 12 there is a headspace 18 in which headspace gases and vapors may accumulate. Since there are gases or vapors accumulating in the headspace 18, it is necessary to vent these gases, because the gases may be explosive or flammable if allowed to accumulate in the headspace 18. These gases present environmental hazards which could conceivably rupture the container comprised of the drum 10 on which the lid 12 is held by circular clamp 14.

In accordance with the principles of the present invention, venting is accomplished by a filter port 20 disposed through the lid 12. It is also necessary to determine the composition of head gases accumulated in the headspace 18. In accordance with the present invention, this is accomplished by a sampling port 22, also inserted in the lid 12. In accordance with the present invention, the filter port 20 and sampling port 22 in combination with the drum 10 provide a method and arrangement for handling transuranic waste 16 having gases which may present an environmental hazard and which must be known, filtered and vented in order to minimize environmental risks.

While transuranic waste is a primary concern with respect to the present invention, the arrangement shown in FIG. 1 is also usable for the storage and transport of other hazardous waste or other hazardous materials, whether the materials are waste material or material to be used for some purpose.

Figure 2:
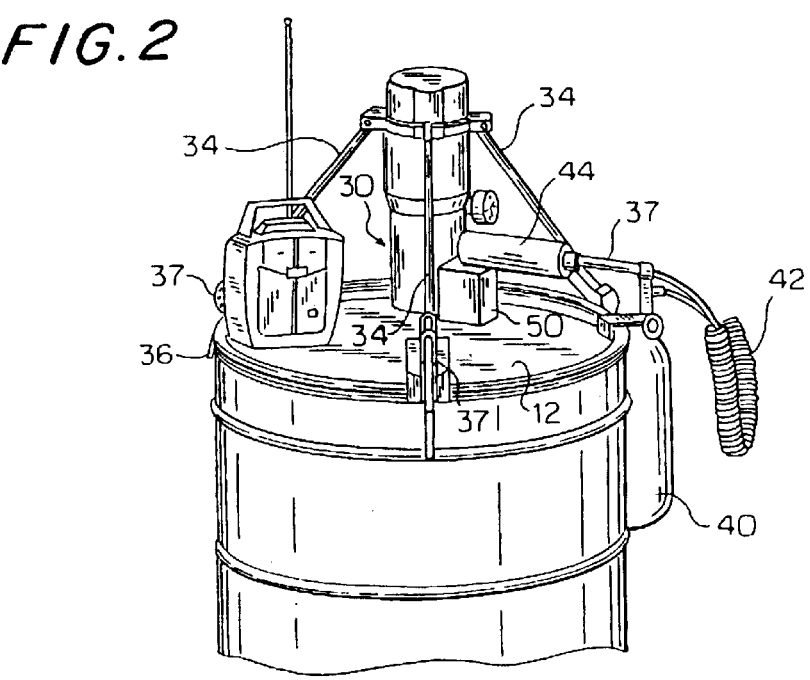
FIG. 2 is a perspective view of a pneumatic gun used to install the sample and filter ports of FIG. 1.

Referring now to FIG. 2, there is shown an arrangement for inserting the filtering and sampling ports 20 and 22 of FIG. 1 wherein drum 10 of FIG. 1 has temporarily mounted thereon a pneumatic gun 30 which drives the ports 20 and 22 configured as punches through the lid 12 of the drum to communicate with the head space 18. Pneumatic gun 30 is preferably a pneumatic gun such as Hitachi Model No. NR-83A which is supported on the lid 12 of the drum by a clamp 32 having three struts 34 pivoted to the clamp at locations 35. The struts are temporarily anchored at the rim 36 of the drum by toggle couplings 37. This arrangement precisely locates the pneumatic gun 30 and holds it in engagement with the lid 12.

Figure 5:
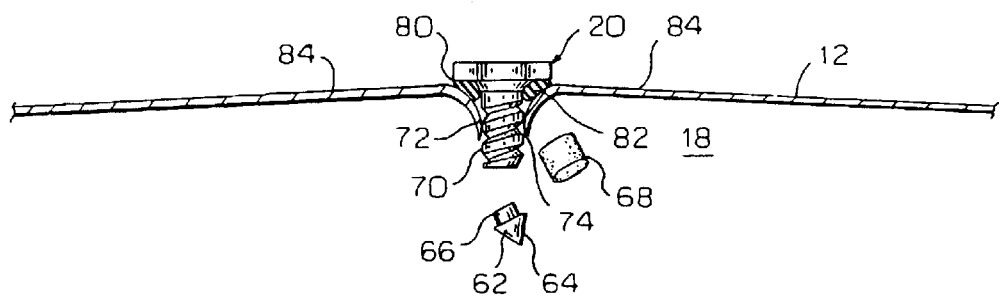
FIG. 5 is a side view of the filter port of FIGS. 3 and 4 installed through a wall of the container as shown in FIGS. 1 and 2.

The pneumatic gun 30 has attached thereto a cylinder of compressed air 40 that has a pneumatic line 42 connected through a charging cylinder 44 to the gun 30. Charging cylinder 44 is connected to an actuator 50 which allows air in the charging cylinder 44 to enter the gun 30 so as to drive a piston downwardly. Since the ports 20 and 22 are configured as punches the piston engages and drives the ports through the lid 12 (as seen in FIGS. 5 and 10). It has been found that the filter and vent ports 20 and 22 can be installed using pneumatic gun pressures in the range of 80 to 120 psi in a fraction of a second so that the escape head gases during installation does not occur, or is so minimal as to be inconsequential.

In accordance with the present invention, the actuator 50 actuated remotely by a radio frequency from a transmitter 39 so that the technician installing the venting and sampling ports is remote from the installation process and thus is not exposed to hazardous material which may be dislodged or released during the pneumatic pulse which punches the ports 20 and 22 through the lid 12.

In accordance with the method of the present invention, the vent port 20 is installed first at a first location radially spaced from the axis 13 of the lid 12. The pneumatic gun 30 is shifted by loosening the toggle couplings 37 and moving pneumatic gun 30 to a location on the other side of the axis aligned with the vent punch 20. The toggle couplings 37 are then tightened to fix the pneumatic gun 30 at a second location and again the pneumatic gun 30 is fired, this time to drive the sampling port 22 through the lid 12. Pneumatic gun 30 is then removed so that the arrangement of filter port 20 and pneumatic port 22 as shown in FIG. 1 occurs.

A sample of headspace gas is then obtained through the sampling port 22 and analyzed. The analysis is done at a laboratory which may be remote from the location of the 55-gallon steel drum 10 to determine the nature of the head space gas, and to determine whether or not materials in the drum must be repackaged or undergo further processing before shipping to a storage location. Typically, the headspace gas sample is placed in a canister and shipped by overnight express to a laboratory for analysis.

Figure 3:
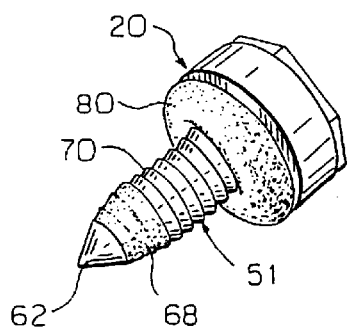
FIG. 3 is a top perspective view of a filter port in accordance with the present invention.
Figure 4:
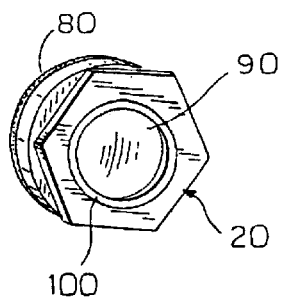
FIG. 4 is a side perspective view of a filter port configured in accordance in the present invention prior to installation thereof.

In order to facilitate the arrangement shown in FIGS. 1 and 2, the filter port 20 shown in FIGS. 3 and 4 and the filter port 22 shown in FIGS. 8 and 9 are configured as punches formed as darts so that they can be rapidly and conveniently forced through and seated within punch holes formed in the lid 12.

Referring now to FIGS. 3–7 where the filter port 20 is shown in detail, the filter port 20 is inserted first so as to vent head gases in the headspace 18 in order to relieve excessive pressure prior to sampling the head gases, should the headspace gas pressure be excessive. As is seen in FIGS. 3–7, the filter port 20 has an annular body 50 having a shank portion 51, a head 53, a first end 52 and a second end 54. A passage 56 extends centrally through the annular body 50, the passage having a first opening 58 and a second opening 60. Inserted with the first opening 58 there is a conical punch point 62 which has pointed portion 64 and a stud portion 66. The stud portion 66 is received in the first opening 58 of the passage 56 and is held in place by a retaining collar 68. The retaining collar 68 is made of plastic and overlies exterior threads 70 on the annular body 50 of the punch, as well as overlaying a portion of the conical portion 64 of the punch point 62.

As is seen in FIG. 5, as the punch point 62 penetrates the lid 12, it is stabilized by the stud 66 which is received in the passage 56. As the filter port 20 is pressed downwardly through the lid 12, the plastic retaining sleeve 68 is pressed against the threads 70 on the annular body 50 by wall 72 which defines the hole 74 through which shank 51 of the body portion 50 passes. The retaining sleeve 58 is severed by the threads 70 because the retaining sleeve 68 is pushed up against the threads by the wall 72. Since the retaining sleeve 68 is located adjacent the head 53 of the shank portion 51, it is carried into the headspace 18 and releases the punch point 62 because its ability to hold the punch point 62 has been negated. Both the punch point 62 and the retaining sleeve 68 then fall away into the headspace 18, so that the opening 58 in the passage 56 of the body 50 communicates directly with the headspace.

Positioned around the shank 51 in a groove 76 beneath the head 53 of the vent port 20 is an O-ring 80 made of a long lasting material such as neoprene. The O-ring 80 seats against a top curved portion 82 of the wall 72 that defines the opening 74 to seal the body member 20 with respect to the top surface 84 of the lid 12. The threads 70 bite into the surface of the wall 72 so as to firmly hold the vent head 20 in place with the O-ring 80 deformed. Thus the vent head 20 is permanently fixed to the lid 12. If for some reason, it is necessary to remove the vent head 20, a hex nut portion 88 is formed on the head 53 so that upon counter-clockwise rotation of the vent head 20, it may be backed out of the opening 74. This requires considerable torque since the lid 12 is made of steel and the threads 70 of the shank portion bite into the wall 72 of the opening 74 with considerable force.

In order to minimize the possibility of sparking, the body 50 of the vent port 20 made of an aluminum-bronze alloy, as is punch point 62.

Figure 6:
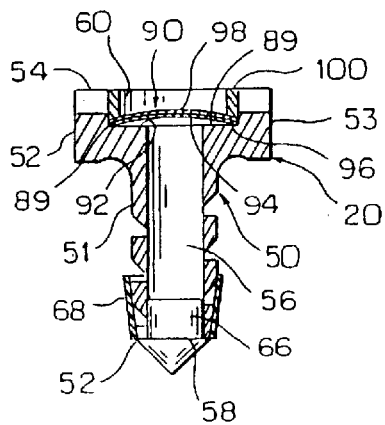
FIG. 6 is an enlarged side elevation of the filter port of FIG. 5.
Figure 7:
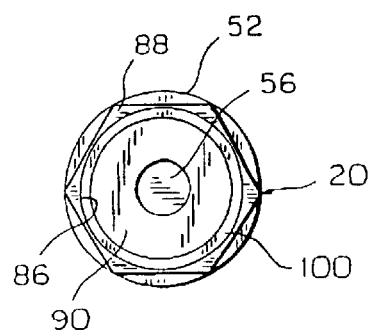
FIG. 7 is a top view of the filter port of FIG. 6.

The vent head 20 and the sampling head 22 are similarly configured with the exception of the passages 56 and 56' respectively, the passage 56 in the vent head 20 of FIGS. 3–7 having a wider step portion 89 at second end 60 configured to receive a filter element 90. Filter element 90 fits on a shoulder 92 within the passage 56 and has a diameter greater than the passage 56. As is seen in FIG. 6, three filter components comprise the filter element 90; the first component being a stainless steel screen support 94 which rests on the shoulder 92; the second component being a polyethylene woven filter media 96, and the third component being a HEPA filter 98 i.e. a Gortex filter which blocks entry of moisture but permits escape of vapors. The entire filter element 90 comprised of the three components 94, 96 and 98 is less than $\frac{1}{8}^{th}$ inch thick and is held in place by an annular stainless steel retainer 100 which has a friction fit or force fit within the widened step portion 89 of the housing.

Filter element 90 meets WIPP, WAC and TRUPACT-II SAR section 1.3.5 requirements, i.e.:

$H_2$ permeability exceeds 3.7 e–o6 mol/s/mol fraction;

has greater than 99.97% removal of 0.45 micron DOP, and has greater than 60 ml/min @<1" water column.

After the vent head 20 is inserted, any head gases which have accumulated in the headspace 18 under pressure pass through the filter 90. Consequently, pressure within the headspace is reduced to the surrounding atmospheric pressure.

Referring now more specifically to FIGS. 8–12, the sampling port 22 is then inserted through the lid 12 at a location which is preferably radially spaced from the vent head 20 location as is seen in FIG. 1. As is stated previously, insertion of the sampling port 22 is accomplished by moving the pneumatic gun 30 so that the sampling port 22 is displaced 180° from the venting port 20. Once the venting port 20 has equalized head space pressure with atmospheric pressure, installation of the sampling port 22 is accomplished without the possible hazard of inserting a closed punch into a closed headspace 18.

Referring now to FIGS. 8–12, sampling port 22 has reference numerals are similar to those of the venting port 20, but with primes. Accordingly, the sampling port 22 is inserted through the lid 12 in substantially the same way as the venting port 20. A substantial difference in structure between the sampling port 22 and venting port 20 is that the sampling port includes in its passage 56' a silicon septa 110 that seals the passage 56' so that ordinarily gas in the headspace 18 can not pass through the passage 56'. The septa seal 110 is disposed between a first set screw 112 that is disposed between the septa 110 and the first open end 58' passage 56' and a second set screw 113 threaded in passage 56'. Passage 56' is threaded down to a shoulder 114 which is engaged by a first set screw 112. The first set screw 112 has a bore 116 extending axially therethrough along the longitudinal axis thereof which communicates with the passage 56' and therefore the first opening 58'. The second set screw 113 has an axial bore 115 similar to bore 116 extending therethrough, and a third set screw 120 is thresded through the bore 56' after the septa seal 110 and second set screw 113 are in place. The third set screw 120 is sealed against a shoulder 122 at the second end 60' of the passage 56' by O-ring 124. The third set screw 120 is solid all the way through and does not include a bore like the bore 116 through the set screw 112 or the bore 115 through the second set screw 113. Consequently, there is a permanent seal of the passage 56' as long as the third set screw 120 is set in place.

Referring now to FIG. 13, in order to sample the gas in headspace 18, the third set screw 120 is backed out by inserting hex wrench in a hexagonal socket 126 to expose the septa seal 110. Hollow needle 130 is then inserted through bore 115 in the second set screw 113, through the septa 110 and through the bore in the set screw 112 to withdraw test samples from the space 18. In accordance with known techniques, the hollow needle 130 is connected to a canister such as a Summa® canister for shipping to a laboratory for analysis. After the head gas sample is taken, the third set screw 120 is rethreaded into the bore 56' to create what can be a permanent seal unless further sampling is needed, in which case the third set screw 120 can be again backed out. Thereafter, the headspace 18 is vented through the aforedescribed venting port 20 in the lid 12.

From the foregoing description, one skilled in the art can easily ascertain the essential characteristics of this invention, and without departing from the spirit and scope thereof, can make various changes and modifications of the invention to adapt it to various usages and conditions.

We claim:

1. A punch for penetrating a wall to access a space behind the wall;

the punch comprising:
an annular body having a shank portion, a head portion, a first end and a second end;
a passage through the annular body, the passage having a first opening and a second opening;
a punch point;
a coupling for detachably retaining the punch point to the first end of the annular body, the coupling releasing the punch point upon inserting the punch point through the wall, whereby the first opening of the passage communicates with the space behind the wall.

2. The punch of claim 1 wherein coupling comprises an element which releases the punch point upon the punch being forced through the wall.

3. The punch of claim 1 wherein the coupling comprises a stud on the punch point which is received in the open end of the passage.

4. The punch of claim 3 wherein the coupling which holds the stud of the punch point in the passage is an element which releases the punch point after the punch point has penetrated the wall.

5. The punch of claim 4 wherein the element is a collar which disengages from the punch point as the punch point passes through the wall.

6. The punch of claim 5 wherein the passage includes a seal therein.

7. The punch of claim 6 wherein the seal comprises a septa seal retained within the passage.

8. The punch of claim 1 wherein the passage includes a seal therein.

9. The punch of claim 8 wherein the seal is a septa seal adapted to permit the passage of a hollow needle therethrough to sample fluid in the space behind the wall.

10. The punch of claim 9 wherein septa seal is axially fixed between two retainers threaded into threads extending into the passage from the second end of the passage.

11. The punch of claim 1 wherein the annular body includes a shoulder intermediate the first and second ends of the body, the shoulder facing the first end.

12. The punch of claim 11 wherein an annular seal engages the shoulder for sealing with the wall.

13. The punch of claim 12 wherein an exterior toothed portion on the shank of the body is disposed between the first end of the body and the annular seal, the exterior toothed portion being adapted to make an interference fit with a concave portion of the wall formed by pushing the punch therethrough.

14. The punch of claim 13 wherein the exterior toothed portion is formed by a helical thread.

15. The punch of claim 1 wherein the passage includes a filter element therein.

16. The punch of claim 15 wherein the filter element is a HEPA filter having $H_2$ permeability that exceeds 3.7 E06 mol/s/mol fraction; removal of 0.45 micron DOP of at least 99.97%, and passes gas at a rate of at least 60 ml/min at less than one inch W.C.

17. The punch of claim 16 wherein the filter element is comprised of a polyethytholene filter media disposed between a stainless steel screen and a semi-permeable membrane.

18. The punch of claim 17 wherein the passage is stepped with a shoulder facing the second end of the passage and wherein the filter element is disposed on the shoulder and retained by an annular retainer which is force fitted in the first end of the passage.

19. The punch of claim 18 wherein the annular body and punch point are made of an aluminum-bronze alloy.

20. The punch point of claim 19 wherein the annular filter retainer is made of aluminum bronze alloy.

* * * * *